US007655051B2

(12) United States Patent
Stark

(10) Patent No.: US 7,655,051 B2
(45) Date of Patent: Feb. 2, 2010

(54) ARTIFICIAL HAND

(76) Inventor: Mark Stark, 10345 Roscommon, St. Louis, MO (US) 63123

( * ) Notice: Subject to any disclaimer, the term of this patent is extended or adjusted under 35 U.S.C. 154(b) by 681 days.

(21) Appl. No.: 11/271,093

(22) Filed: Nov. 10, 2005

(65) Prior Publication Data

US 2006/0129248 A1 Jun. 15, 2006

Related U.S. Application Data

(60) Provisional application No. 60/627,560, filed on Nov. 12, 2004.

(51) Int. Cl.
*A61F 2/54* (2006.01)
(52) U.S. Cl. .......................... 623/64; 623/63
(58) Field of Classification Search ............ 623/63, 623/64
See application file for complete search history.

(56) References Cited

U.S. PATENT DOCUMENTS

| 1,484,913 | A | * | 2/1924 | Surry | 623/63 |
|---|---|---|---|---|---|
| 1,742,269 | A | | 1/1930 | McElroy | |
| 1,929,926 | A | * | 10/1933 | Laherty | 623/64 |
| 2,285,885 | A | | 6/1942 | Becker | |
| 2,435,614 | A | * | 2/1948 | Tureman, Jr. | 623/64 |
| 2,500,614 | A | | 3/1950 | Lohmann | |
| 2,542,316 | A | * | 2/1951 | Farrar, Jr. | 623/61 |
| 2,556,524 | A | * | 6/1951 | Drennon | 623/64 |
| 2,561,383 | A | | 7/1951 | Larkins | |
| 2,853,711 | A | * | 9/1958 | Becker | 623/63 |
| 4,258,441 | A | * | 3/1981 | Bell | 623/64 |
| 4,315,650 | A | | 2/1982 | Yoshida | |
| 4,685,924 | A | | 8/1987 | Massey | |
| 4,685,929 | A | * | 8/1987 | Monestier | 623/64 |
| 4,865,613 | A | * | 9/1989 | Rizzo | 623/65 |
| 5,080,681 | A | | 1/1992 | Erb | |
| 5,200,679 | A | | 4/1993 | Graham | |
| 2006/0224249 | A1 | * | 10/2006 | Winfrey | 623/64 |

FOREIGN PATENT DOCUMENTS

FR 2432303 A1 * 2/1980

* cited by examiner

*Primary Examiner*—Bruce E Snow
*Assistant Examiner*—Melissa Montano
(74) *Attorney, Agent, or Firm*—Greensfelder, Hemker & Gale, P.C.; Linda L. Lewis

(57) ABSTRACT

An artificial hands having more than one articulated digit wherein the digits are biased in a closed position by springs, and digits are opened by a cord attached to the dorsal side of the digit and a lever, wherein the lever is rotatably mounted to an anchoring plate and pulled by a cable; wherein the cable is pulled manually by means of a shoulder strap, or electronically by a motor.

19 Claims, 7 Drawing Sheets

ARTIFICIAL HAND

CROSS-REFERENCE TO RELATED APPLICATION

The present invention claims the benefit of U.S. Provisional Application entitled "Artificial Hand", Ser. No. 60/627,560, filed Nov. 12, 2004, which is herein incorporated by reference.

THE FIELD OF THE INVENTION

The present invention relates to prosthetic devices, robotic hands and claw manipulators. More specifically, the present invention relates to artificial hands having more than one articulated digit wherein the digits are biased in a closed position by springs, and each digit is opened by a cord attached to the dorsal side of the digit and a lever, wherein the lever is rotatably mounted to an anchoring plate and pulled by a cable.

BACKGROUND OF THE INVENTION

Artificial hands are well-known in the art. Many artificial hands are biased open, they are at rest in the open position. These hands have an artificial look, in that normal human hands rest in a curved, closed position rather than a flat, spread open position. Further, many of the uses of for an artificial hand are for the closed position, such as gripping, lifting or carrying an object.

Artificial hands that are biased closed are also disclosed in the art. However, these devices are typically complicated, expensive, heavy and difficult to repair. Such hands are disclosed in U.S. Pat. Nos. 5,200,679, 4,685,924, 2,561,383, 2,500,614, 2,285,885 and 1,742,269. The present invention is operated without the use of motors, is simple to construct and repair, is robust, and provides the user with the ability to grasp and lift objects such as a glass to drink from or even to catch a ball.

A mechanical hand amusement device is disclosed in U.S. Pat. No. 4,315,650 that discloses articulated digits biased in the open position. The digits are flexed by a flexible strap that is moved by a hand grip. U.S. Pat. No. 4,315,650 fails to disclose the present invention which provides the user with the ability to grasp and carry objects without the use of a human hand, wherein the prosthetic device has more than one articulated joints.

DISCLOSURE OF THE INVENTION

The present invention relates to prosthetic or robotic hands having more than one articulated digit wherein the digits are biased in a closed position by springs, the digits are attached to a base plate and a cord is attached to each digit on the dorsal side and a lever, wherein the lever is rotatably mounted to the base plate and pulled by a cable attached to the lever to activate the digits and move them from the closed position to the open position.

The present invention further contemplates a prosthetic hand having four digits and a thumb, where the digits and thumb are biased in the closed position by coil springs at the joints of the digits and thumb, so that the thumb and digits encircle and close in a manner suitable for grasping an object. The hand is operated by means of a pull cable attached to a lever rotatably mounted on the base plate such that when the cable is pulled, the lever pulls the cords attached to the digits and thumb and moves them to the open position. Such action allows the grasping of an object when the pull cable is released, releasing the lever, thereby releasing the cords to the digits and thumb, returning them to the closed position. Since each digit has a cord and springs, when an object is grasped, the digits close around the object, regardless of its shape, conforming to its shape and providing a natural appearance of the hand, rather than an artificial appearance.

The pull cable of the present invention can be activated by mechanical means or human means. In a preferred embodiment, the pull cord is activated by a shoulder harness worn by the user, who, by movement of his or her shoulders can cause tension on the cord thereby opening the prosthetic hand, or relax tension on the cord, thereby closing the prosthetic hand. All of the digits are activated simultaneously. However, in the event that the user does not have that capability, mechanical means such as electric motors can be used to pull or relax the cable.

In a preferred embodiment, the artificial hand can be covered by a glove or other covering to give it a natural appearance. Further, the digits can be covered by a synthetic material to give it greater gripping ability. A polymeric, resinous or rubber-like material could be used to provide a gripping surface for the hand.

BRIEF DESCRIPTION OF THE DRAWINGS

Referring to FIG. 1, artificial hand 1 is in the open, activated position. It comprises a base plate 10 having rotatably attached to it four digits 40 and a thumb 39. The base plate 10 has a dorsal side 20 and a palmar side 30. Lever 50 is rotatably attached to the dorsal side 20 at pivot point 60. Attached to lever 50 at attachment point 71 is pull cable 70. The construction material of the artificial hand can be metal, plastic, even wood. The construction material is preferably strong, durable, light and inexpensive. A preferred material is durable plastic, or light-weight metal, such as aluminum.

Figure 1:
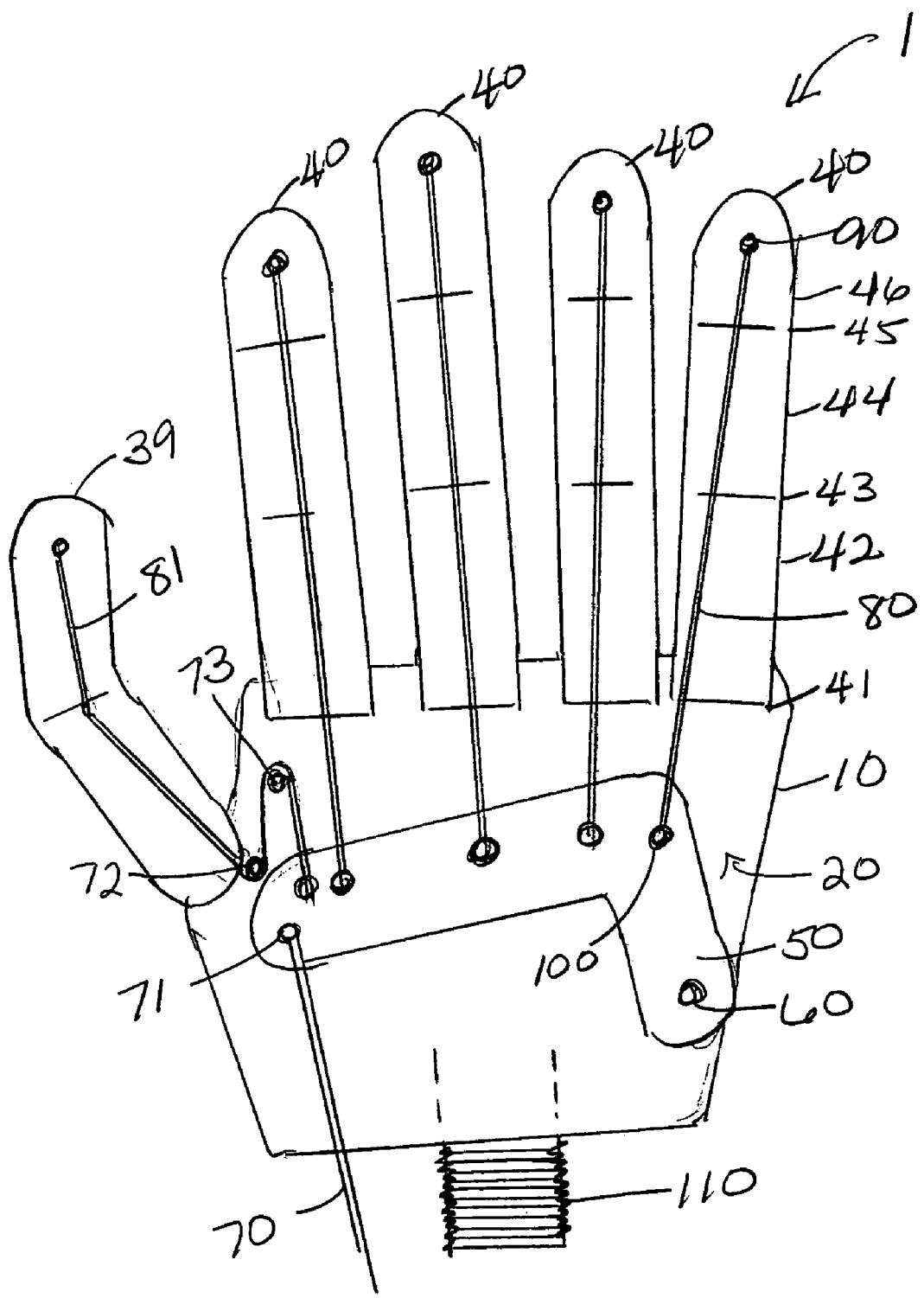
FIG. 1 is a top dorsal view of the artificial hand in an open, activated position.

The digits 40 of the artificial hand 1 are articulated, and in this embodiment have three segments. The thumb 39 has two segments. The three digit segments are 42, 44 and 46. The segments are connected by flexible hinges 43 and 45. Further the digits 40 attached to the base plate 10 by flexible hinges 41. At the distal end of the digits are attachment points 90 where cords 80 are attached to the digits 40. The cords 80 traverse the dorsal side of the digits, and attach to lever 50 at attachment points 100. The cord 81 of the thumb is lengthened to provide greater range of movement by lengthening cord 81 and looping it around posts 72 and 73. In an embodiment of the invention (not shown), the cords 80 are attached to the second segment 44 of the digits, rather than the third segment 46. This causes segments 42 and 44 only to open when the hand is activated by pulling cable 70.

In FIG. 1, the artificial hand 1 is shown in the open (activated) position. The hand 1 is activated and opened by pulling on cable 70, which causes the lever 50 to rotate at pivot point 60. When the lever rotates, the cords 80 rotatably pull the digits from the closed position to the open straight position. Likewise, when the lever 50 rotates, cord 81 of the thumb rotatably pulls the thumb from the closed into the open position.

Figure 2:
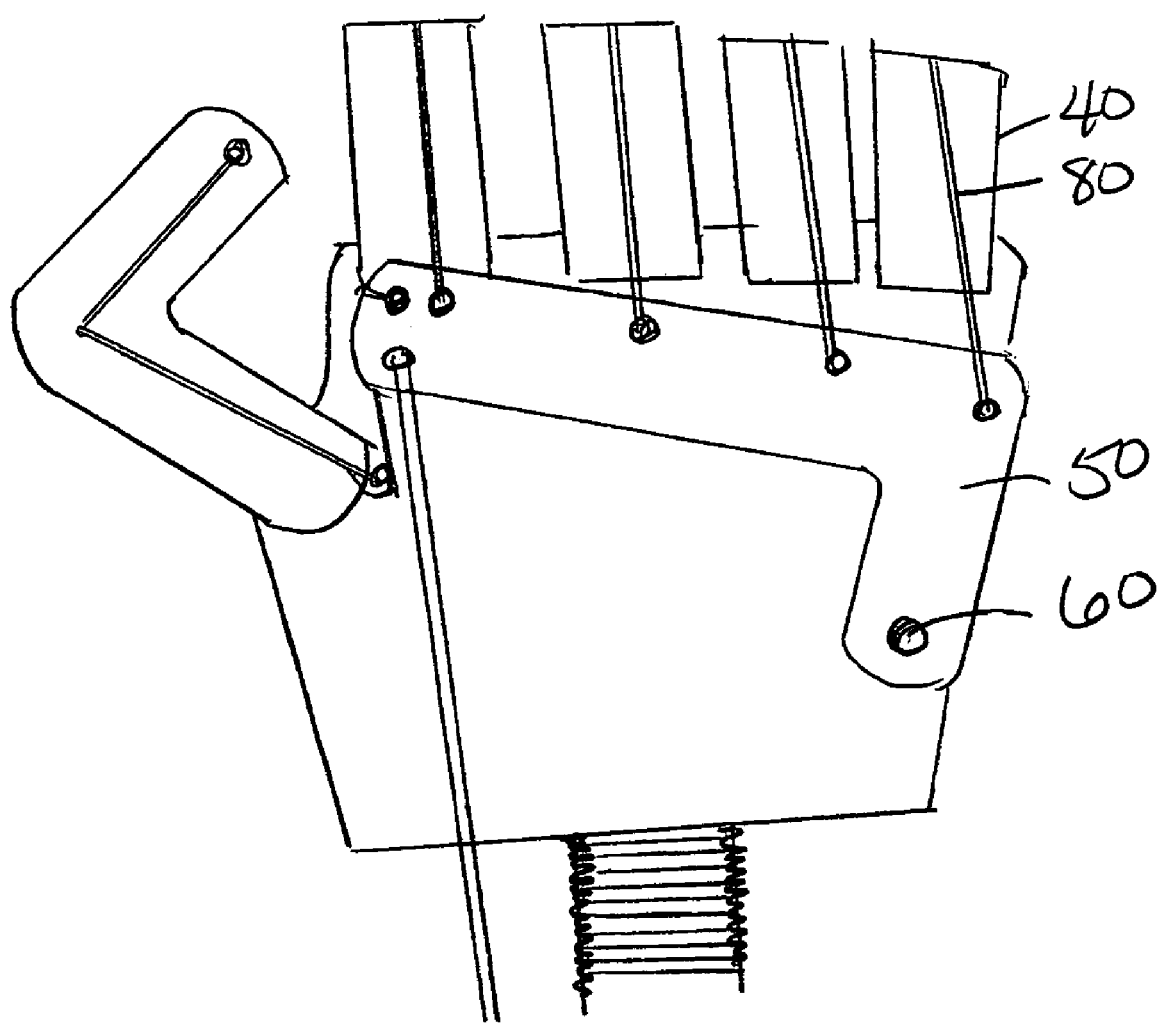
FIG. 2 is a top dorsal view of the artificial hand in a closed position.

Referring to FIG. 2, the artificial hand 1 is shown in the inactivated, closed position. The cable 70 is released, and the digits 40 and the thumb 39 are in the closed position. The digits are pulled into the closed position by springs 120 at each operating joint (see FIG. 4). The lever 50 has pivoted forward at pivot point 60, allowing the cords 80 and 81 to move toward the distal end of the digits 40 and thumb 39, allowing them to curl into the closed position.

Figure 4:
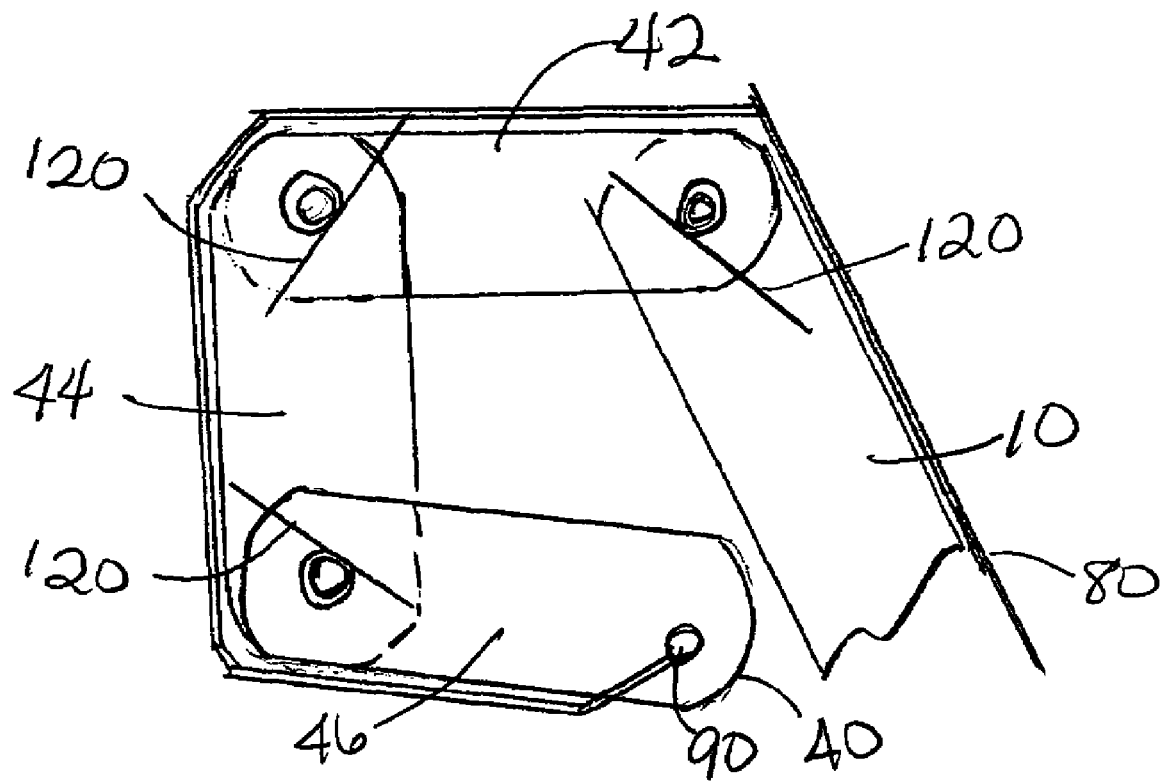
FIG. 4 is a side view of a digit of the artificial hand in a closed position.

Referring to FIG. 4, the digits in the closed position are pulled into position by coil springs 120. When the digits are in the closed position, the coil springs are partially compressed (more relaxed position). When the digits are in the open position due to pulling on cable 70 (see FIG. 2), which displace lever 50, the springs at each operating joint 120 are in the extended position (more compressed) and are pulling against the segments 42, 44 and 46.

Figure 3:
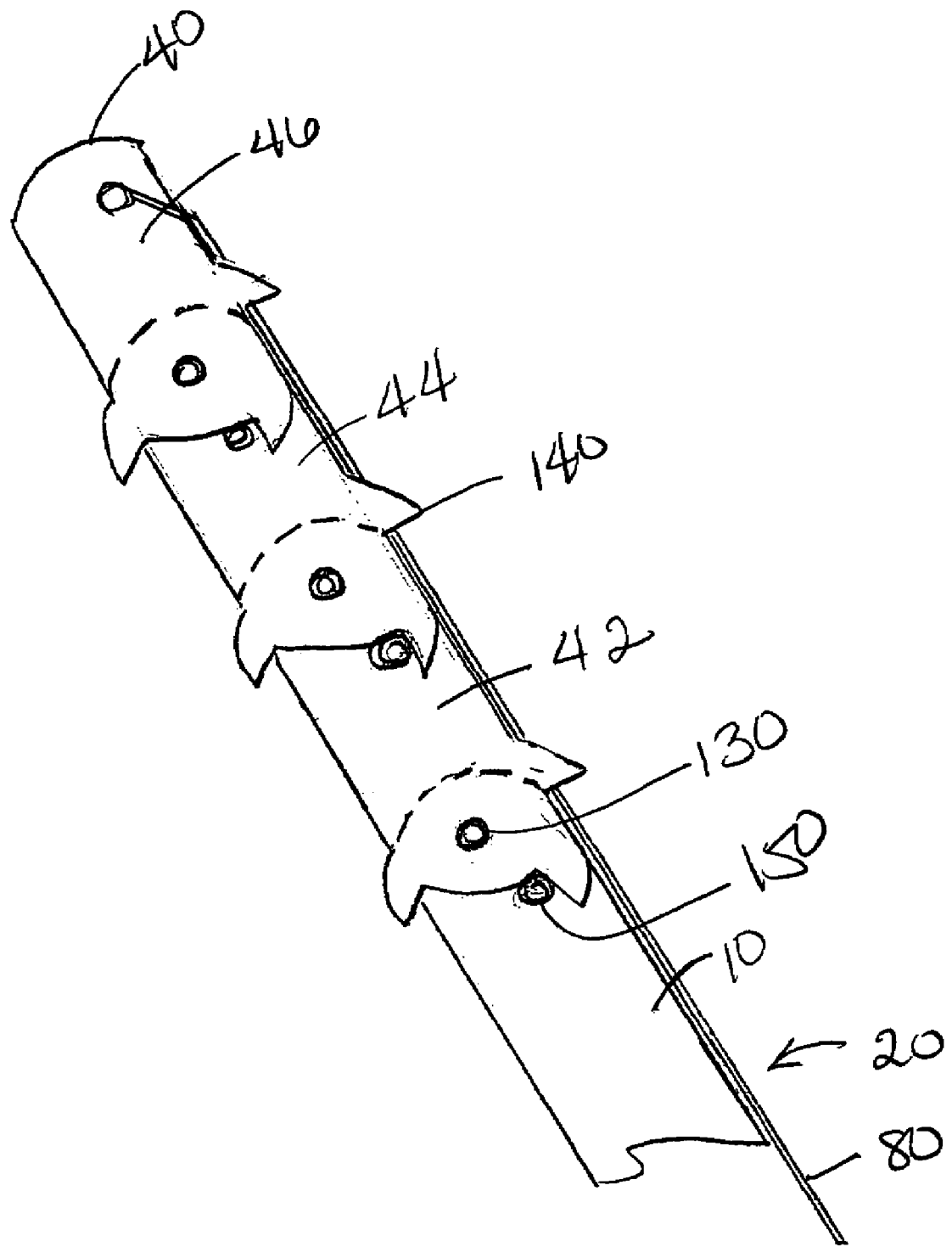
FIG. 3 is a side view of a digit of the artificial hand in an open, activated position.

Referring to FIG. 3, digit 40 has segments 42, 44 and 46 rotatably joined by digit pivots 130. Further, segments 42 and 44, as well as base plate 10 have stops 150 which engage with the base of segments 42, 44 and 46 to limit rotation, and to prevent the digit from flexing toward the dorsal side 20 of the artificial hand. Further, the segments have cord guides 140 which serve to guide the cord 80 along the dorsal side 20 of the digits.

At the base of the base plate is connector 110 (see FIG. 1), which is used to attach the artificial hand 1 to a prosthetic mounting. A typical connector is a bolt that simply screws into the mounting.

Figure 5:
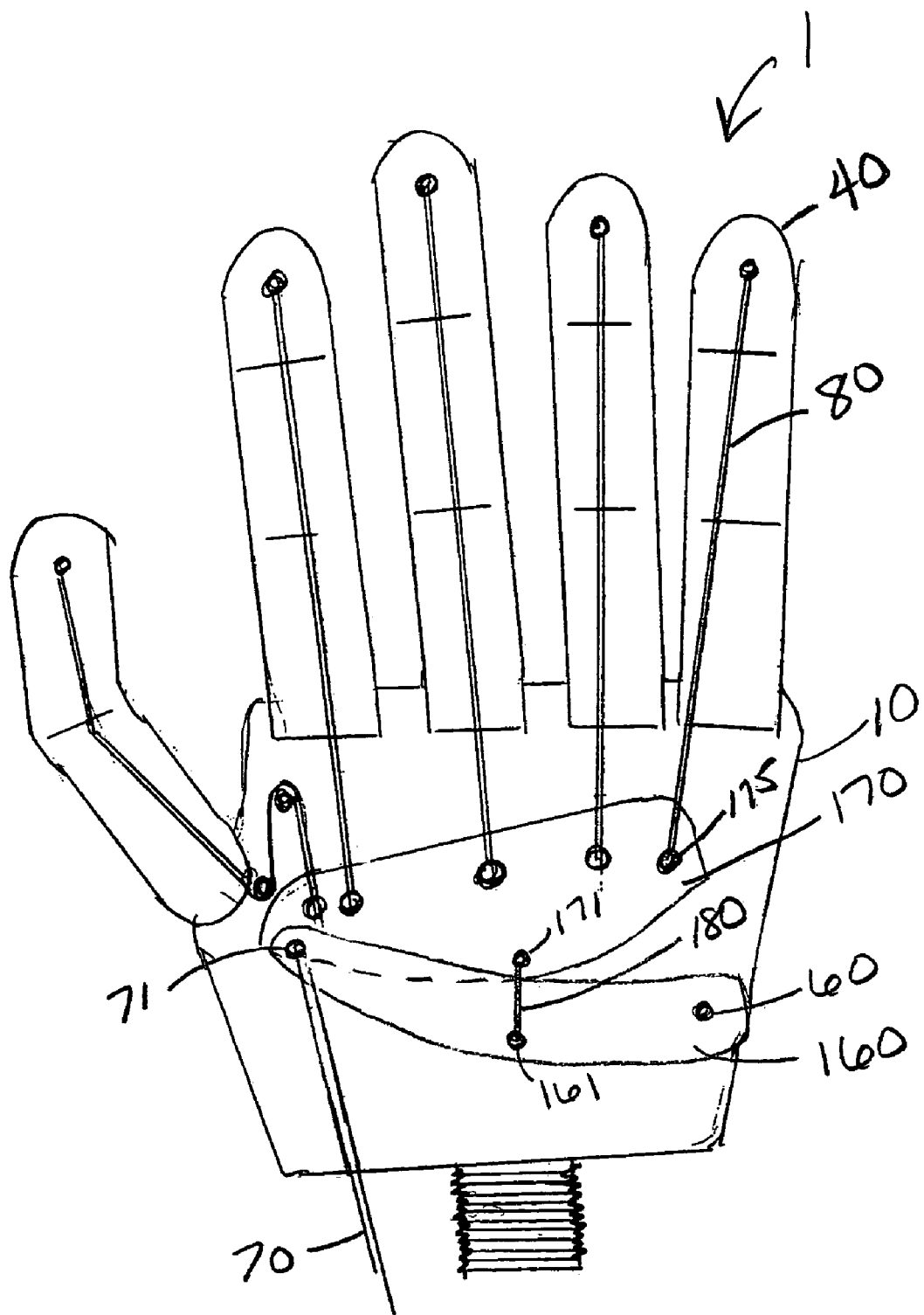
FIG. 5 is a second embodiment of a top dorsal view of the artificial hand in an open, activated position.

FIG. 5 is a second embodiment of the invention in the activated position, wherein the prosthetic hand has a lever 160 attached rotatably at pivot point 60 to the base plate 10. The lever 160 is further attached to the pull cable 70 at attachment point 71. Digit plate 170 is attached by cords 80 to the distal ends of the digits 40 and thumb 39 at attachment points 175. The lever 160 is attached to the digit plate 170 by lever cable 180 at attachment points 161 and 171.

According to this second embodiment, when cable 70 is pulled lever 160 rotates around pivot point 60, digit plate 170 moves, pulled by lever cable 180, retracting cords 80 and 81 to open digits 40 and thumb 39. As indicated by the dashed lines of FIG. 5, the digit plate 170 moves beneath lever 160. The advantage of this second embodiment is that the lever 160 and the digit plate 170 can be designed such that each digit is moved the same distance. Further, the position of the pull cable 70 and the lever cable 180 is designed that there is a ratio of distances moved by each when the artificial hand 1 is activated, such that the force generated is increased.

Figure 6:
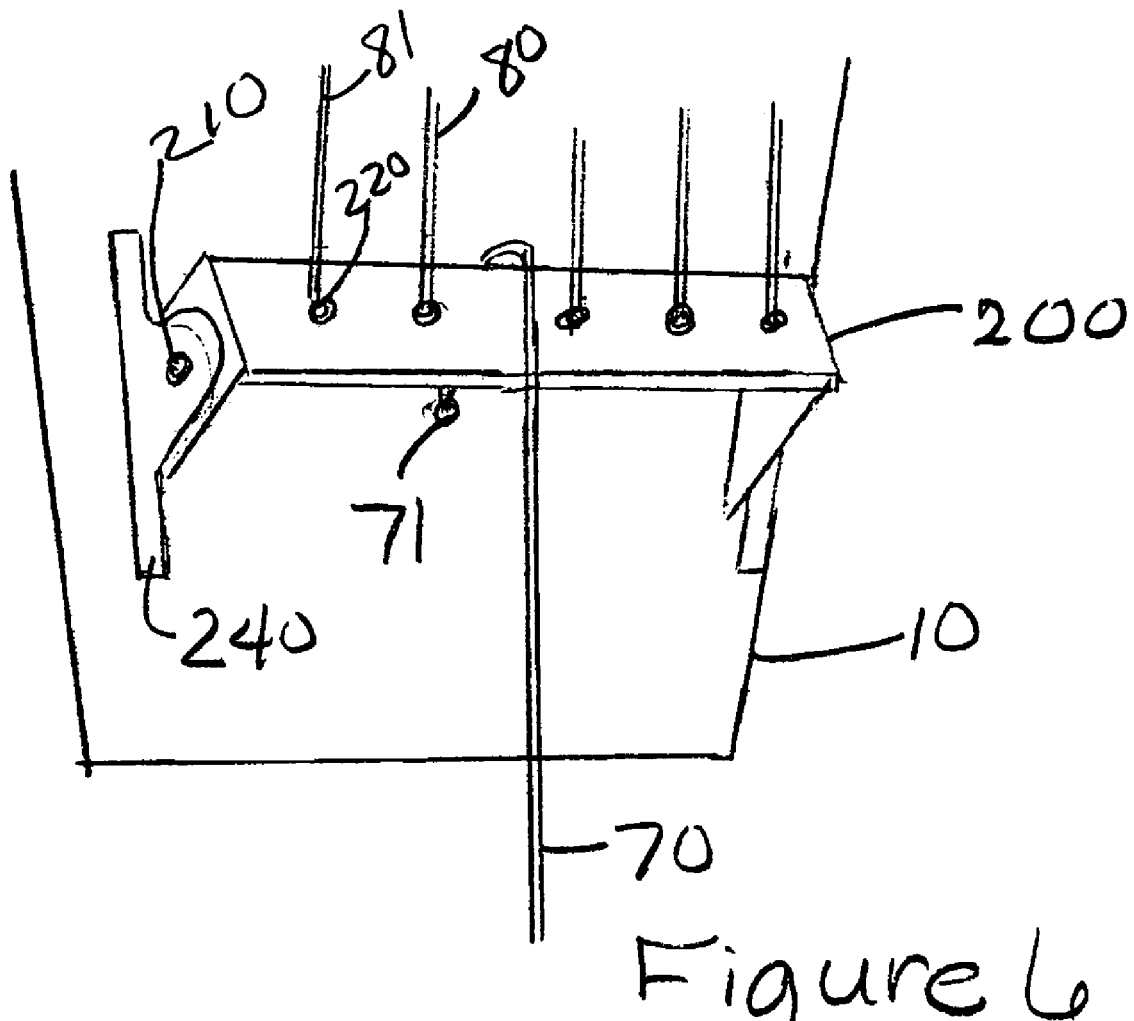
FIG. 6 is a third embodiment of an elevated partial side view of the dorsal side of the artificial hand in an partially activated position.
Figure 7:
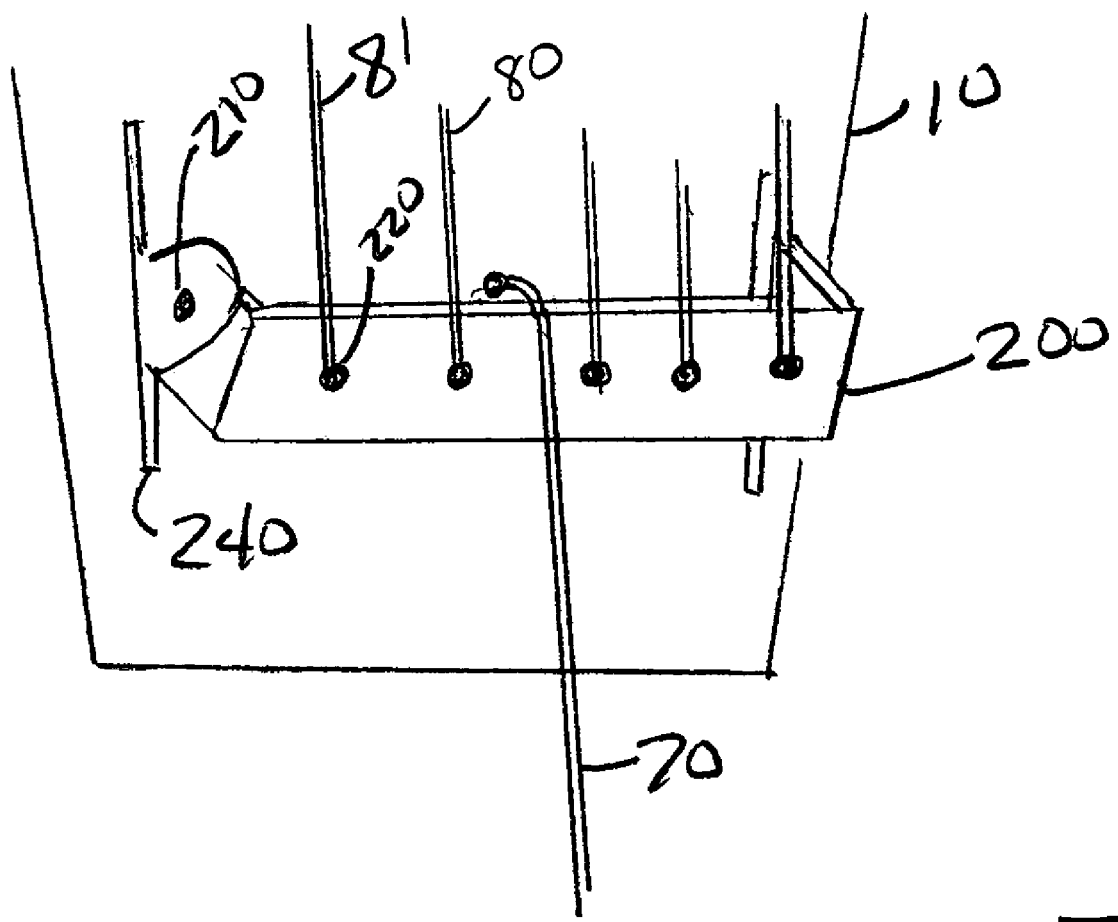
FIG. 7 is a third embodiment of an elevated partial side view of the dorsal side of the artificial hand in a fully activated position.

FIG. 6 is a third embodiment of the invention, showing lever 200 partially activated. Lever 200 is pivotally mounted on base plate 10, with one or more lever mounts 240. Pull cable 70, which is attached to base plate 10 at 71, passes over lever 200 and engages lever 200 along a cable guide (not shown). Optionally, pull cable 70 is directly attached to lever 200 (not shown). Cords 80 and 81 are attached to lever 200 at cord attachment points 220. As shown in FIG. 7, when lever 200 is activated by pulling cable 70, the lever rotates around pivot point 210, causing cords 80 and 81 to be retracted, thereby opening the digits of the artificial hand. When pull cable 70 is released, cords 80 and 81 are released, and the digits return to the biased closed position. As with the second embodiment, the design of lever 200 is such that the force generated in the moving of the lever is increased.

The above invention is not limited to the embodiments, nor do they limit the claims in any manner.

The invention claimed is:

1. An artificial hand comprising
   a base plate;
   more than one articulated digits wherein the digits have one or more joint and wherein the digits are rotatably attached to the base plate having a dorsal side and a palmar side;
   a coil spring attached at each joint;
   each digit having a cord having a first and second end, where the first end is attached to the digit on the dorsal side;
   a lever rotatably attached to the base plate wherein the second end of the one or more cords is attached directly or indirectly to the lever; and
   a pull cable attached to the lever;
   wherein one spring is attached at each joint such that when the springs are relaxed the digits are in the closed position toward the palmar side of the hand; and
   wherein when the pull cable is pulled, the lever rotates, pulling the cords which pull the digits from the closed position to the open position, thereby activating the artificial hand.

2. The artificial hand of claim 1, wherein the base plate and digits are made of metal and/or plastic.

3. The artificial hand of claim 1, wherein the cord is attached to the digits on the distal end of the digits.

4. The artificial hand of claim 1, wherein there are four digits and one thumb attached to the base plate.

5. The artificial hand of claim 4, wherein the four digits have a first, second and third segment, and the thumb has a first and a second segment.

6. The artificial hand of claim 5, wherein the cord is attached to the second segment of the digits.

7. The artificial hand of claim 1, wherein the lever is attached to the base plate by two attachment points, and rotates at two pivot points, such that each digit moves about the same distance, and the force generated is greater than a lever having one pivot point.

8. The artificial hand of claim 1, wherein the lever engages with a digit plate to retract the cords and activate the hand.

9. The artificial hand of claim 1, wherein the pull cable is attached to a shoulder harness and the hand is activated by movement of the shoulder.

10. The artificial hand of claim 1, wherein the cable is attached to a motor and the hand is activated by the motor.

11. An artificial hand comprising
    a base plate;
    four articulated digits and one articulated thumb rotatably attached to the base plate having a dorsal side and a palmar side;
    wherein each digit has a first, second and third segment between three joints, and the thumb has a first and second segment between two joints;
    wherein each joint has a springs coil spring attached thereto;
    each digit having a cord having a first and second end, where the first end is attached to the digit on the dorsal side at the middle;
    the thumb having a cord having a first and second end, where the first end is attached to the thumb on the dorsal side at the distal end of the thumb;

a lever rotatably attached to the base plate wherein the second end of the cords are attached directly or indirectly to the lever; and a pull cable attached to the lever;

wherein the springs are attached to the digits such that when they are relaxed the digits are in the closed position toward the palmar side of the hand; and wherein when the pull cable is pulled, the lever rotates, pulling the cords which pull the digits from the closed position to the open position, thereby activating the artificial hand.

12. The artificial hand of claim 11, wherein the base plates and digits are made of metal and/or plastic.

13. The artificial hand of claim 11, wherein the base plates and digits are made of aluminum and/or plastic.

14. The artificial hand of claim 11, wherein the lever is attached to the base plate by two attachment points, and rotates at two pivot points, such that each digit moves about the same distance, and the force generated is greater than a lever having one pivot point.

15. The artificial hand of claim 11, wherein the lever engages with a digit plate to retract the cords and activate the hand.

16. The artificial hand of claim 11, wherein the cable is attached to a shoulder harness and the hand is activated by movement of the shoulder.

17. The artificial hand of claim 11, wherein the cable is attached to a motor and the hand is activated by the motor.

18. The artificial hand of claim 11, wherein the hand is covered by a glove.

19. The artificial hand of claim 11, wherein the hand is covered by a synthetic material that gave the appearance of skin.

* * * * *